United States Patent [19]
Kuperman

[11] Patent Number: 5,658,143
[45] Date of Patent: Aug. 19, 1997

[54] DENTAL ARTICULATOR HAVING DOWEL PINS AND SUPPORT PINS

[76] Inventor: Tal Kuperman, 69-28 140th St., Kew Garden Hills, N.Y. 11367

[21] Appl. No.: 500,803

[22] Filed: Jul. 13, 1995

[51] Int. Cl.⁶ .................... A61C 11/00; A61C 19/00
[52] U.S. Cl. .................................. 433/60; 433/74
[58] Field of Search .................... 433/60, 74, 213, 433/34

[56] References Cited

U.S. PATENT DOCUMENTS

| | | | |
|---|---|---|---|
| 3,932,939 | 1/1976 | Weissman | 433/213 |
| 3,937,773 | 2/1976 | Huffman | 433/213 |
| 4,021,916 | 5/1977 | Spalten | 433/74 |
| 4,127,939 | 12/1978 | Samuel et al. | 433/74 |
| 4,265,619 | 5/1981 | Lucki et al. | 433/74 |
| 4,398,884 | 8/1983 | Huffman | 433/213 |
| 4,449,931 | 5/1984 | Saito | 433/74 |
| 4,917,347 | 4/1990 | Fenick | 433/74 |
| 5,466,152 | 11/1995 | Walter | 433/74 |

*Primary Examiner*—Cary E. O'Connor
*Attorney, Agent, or Firm*—Ezra Sutton

[57] ABSTRACT

A dental articulator (10) having a first arch (12) for receiving a dental cast of teeth having a first grid pattern (30) that includes a first plurality of dowel pin holes (60) that define multiple dowel pin locations for receiving a first plurality of dowel pins (34), and a first plurality of support pin holes (62) that define multiple support pin locations for receiving a first plurality of support pins (64) where in the dowel pin locations and the support pin locations are spaced apart such that a die may be held in place within the first arch by one or more of the first plurality of dowel pins and by one or more of the first plurality of support pins to prevent movement or rotation of the die. There is a second arch (14) for receiving a dental cast of teeth having a second grid pattern (32) that includes a second plurality of dowel pin holes (60') that define multiple dowel pin locations for receiving a second plurality of dowel pins (34'), and a second plurality of support pin holes (62') that define multiple support pin locations for receiving a second plurality of support pins (64'), wherein the dowel pin locations and the support pin locations are spaced apart such that a die may be held in place within the second arch by one or more of the second plurality of dowel pins and by one or more of the second plurality of support pins to prevent movement or rotation of the die. The first arch is hingedly connected to the second arch by a hinge connection (40) to allow articulating movement of the first and second arches (12 and 14) with respect to each other.

22 Claims, 15 Drawing Sheets

DENTAL ARTICULATOR HAVING DOWEL PINS AND SUPPORT PINS

FIELD OF THE INVENTION

This invention relates to a new type of dental articulator that is used to make dental prosthesis elements such as, a denture, a crown, a bridge, a cap, an inlay, an onlay, a laminate, and the like. More particularly, this invention relates to a dental articulator that securely holds the prosthesis element in place without movement while the dentist or dental technician works on that prosthetic element.

BACKGROUND OF THE INVENTION

Dental articulators are used by dentists and/or dental technicians to help make a given dental prosthesis like a denture, crown, cap, bridge or an inlay, etc. A dental articulator simulates the movement of the human jaw. Dental articulators vary in design from a simple hinge component to a complex anatomical simulator which shows the movement of the two lower mandibular condyles (the lower jaw bone). Depending upon the needs of the dentist and/or dental technician and the extent of dental prosthesis work being done on the patient, the complexity of a dental articulator design varies with the difficulty of the prosthesis element needed by a given patient,. In general, dental articulators assist the dentist and/or dental technician in preparing an accurately fitting dental prosthesis for a patient with a minimal amount of labor, costs, materials and patients' time at the office or lab.

There exist a need for a simple dental articulator that has more accuracy, more stabilization of the prosthesis element being worked on, without shifting or movement of the prosthesis dies in the lab/work area while being worked on this would give the dentist a very accurately fitting dental prosthetic, like a dental crown, while minimizing the amount of time the dentist has to work in the patients' mouth to fit the crown on the defective tooth being repaired.

DESCRIPTION OF THE PRIOR ART

Dental articulators of various designs and materials of construction have been disclosed in the prior art. For example, U.S. Pat. No. 5,360,367 discloses a dental articulator comprising a series of hinged elements in the form of connecting members having spigots and socket joints therein. U.S. Pat. No. 5,403,185 discloses a dental articulator comprising first and second trays having a plurality of holes each for receiving a single pin for supporting each tooth of the model cast. The Accu Bite Company of East Lansing, Mich. is selling the W.O.W. articulator which has a plurality of dowel holes for receiving dowel pins so that each die is held in place by only one dowel pin. Such an arrangement allows for movement of the die.

The prior art does not teach the use of a plurality of support pins in addition to dowel pins, within the dental articulator for supporting and holding an individual die in place after the model cast has been cut or sawed. Prior art dental articulators have had problems in the shifting or rocking movement of the molded cast or dies while being worked on in the lab. This shifting and rocking motion of the prosthetic die causes decreased accuracy in fitting the dental prosthetic being worked on, thereby increasing the amount of time in the lab to achieve a more accurate product, and also causes the dentist to spend an increased amount of time working in the patients' mouth to correct any minor or major defects in fitting the prosthesis element being worked.

Accordingly, it is an object of the present invention to provide a dental articulator that more securely holds the prosthesis die element being worked on, such that there is no rocking or shifting movement of the prosthesis die element being worked on.

Another object of the present invention is to provide a dental articulator that increases the accuracy of construction of the prosthesis die element being worked on with a minimal amount of time, labor, and cost thereby minimizing the patients' dental costs.

Another object of the present invention is to provide a dental articulator that is easy to handle and work with and that is light weight, durable and universal, such that the articulator can be used for various types of dental prosthesis elements, such as, dentures, crowns, caps, bridges, inlays, onlays, and the like.

A further object of the present invention is to provide a dental articulator that can be mass produce in an automated and economical manner, and is also cost effective.

SUMMARY OF THE INVENTION

In accordance with the present invention, there is provided an improved dental articulator for making dental prosthesis elements such as a denture, a crown, a bridge, and the like. The dental articulator comprises an upper and lower arch each for receiving a dental cast of teeth and each having a grid pattern that includes a plurality of dowel pin holes that define multiple dowel pin locations for receiving a plurality of dowel pins, and a plurality of support pin holes that define multiple pin locations for receiving a plurality of support pins. These dowel pin and support pin locations are spaced apart such that each die may be held in place within the upper and lower arches by a plurality of dowel pins and by a plurality of support pins to prevent movement or rotation of the individual die or dies.

The dental articulator also has inner and outer ridges located on the die receiving surfaces of the upper and lower arches for providing additional support to an individual die or dies to prevent movement or rotation thereof.

The dental articulator can be made from materials such as plastic, aluminum, rubber, or fiberglass. The dowel pins and support pins can be made from materials such as brass, aluminum, stainless steel, or ceramic. The support pins are embedded in the die receiving surfaces and are secured by the use of an epoxy glue.

BRIEF DESCRIPTION OF THE DRAWINGS

Further objects, features, and advantages of the present invention will become apparent upon consideration of the detailed description of the presently-preferred embodiments, when taken in conjunction with the accompanying drawings wherein.

DETAILED DESCRIPTION OF THE PREFERRED EMBODIMENTS

Figure 1:
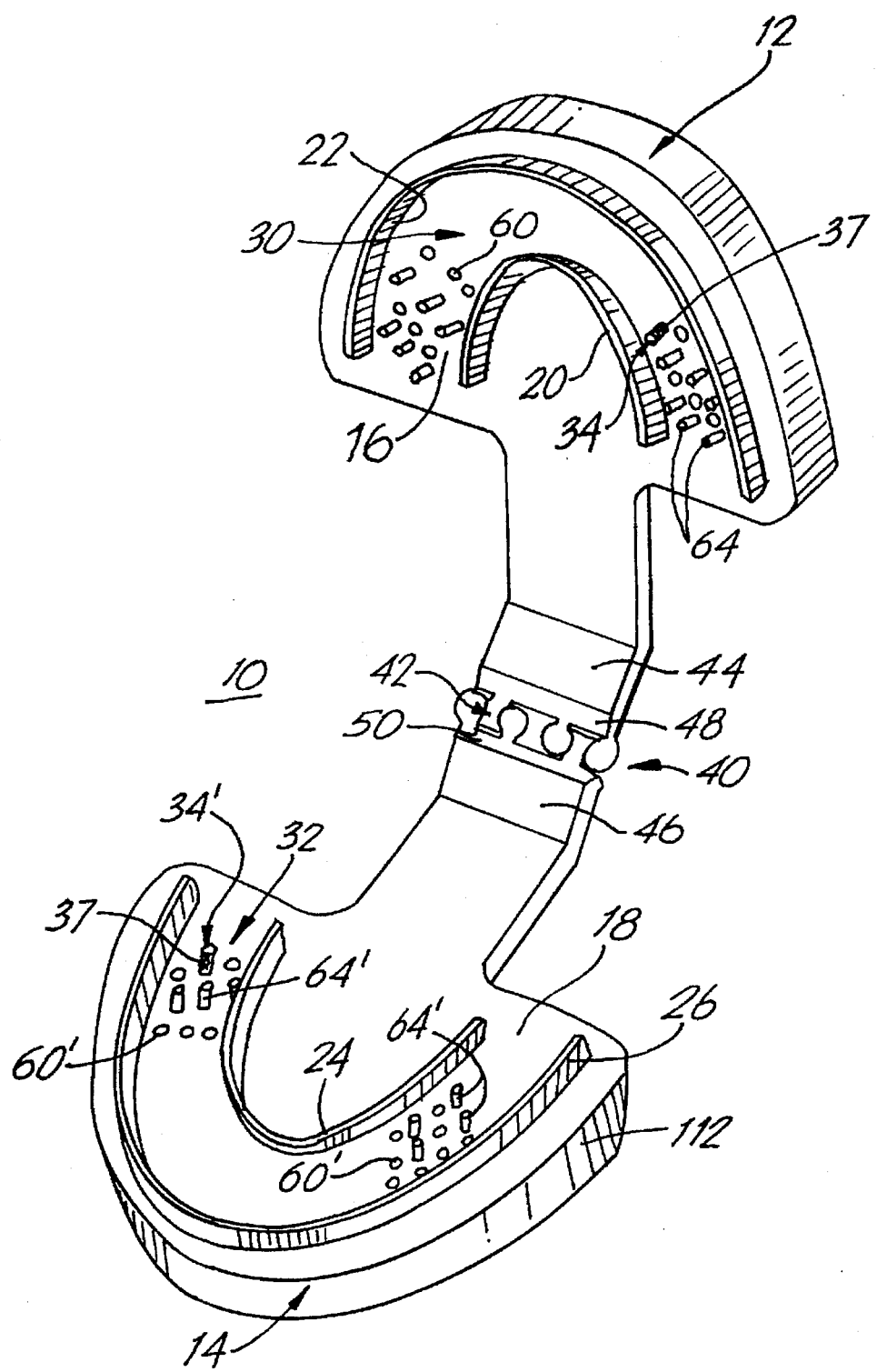
FIG. 1 is a perspective view of the dental articulator of the present invention showing it in its assembled state.
Figure 3:
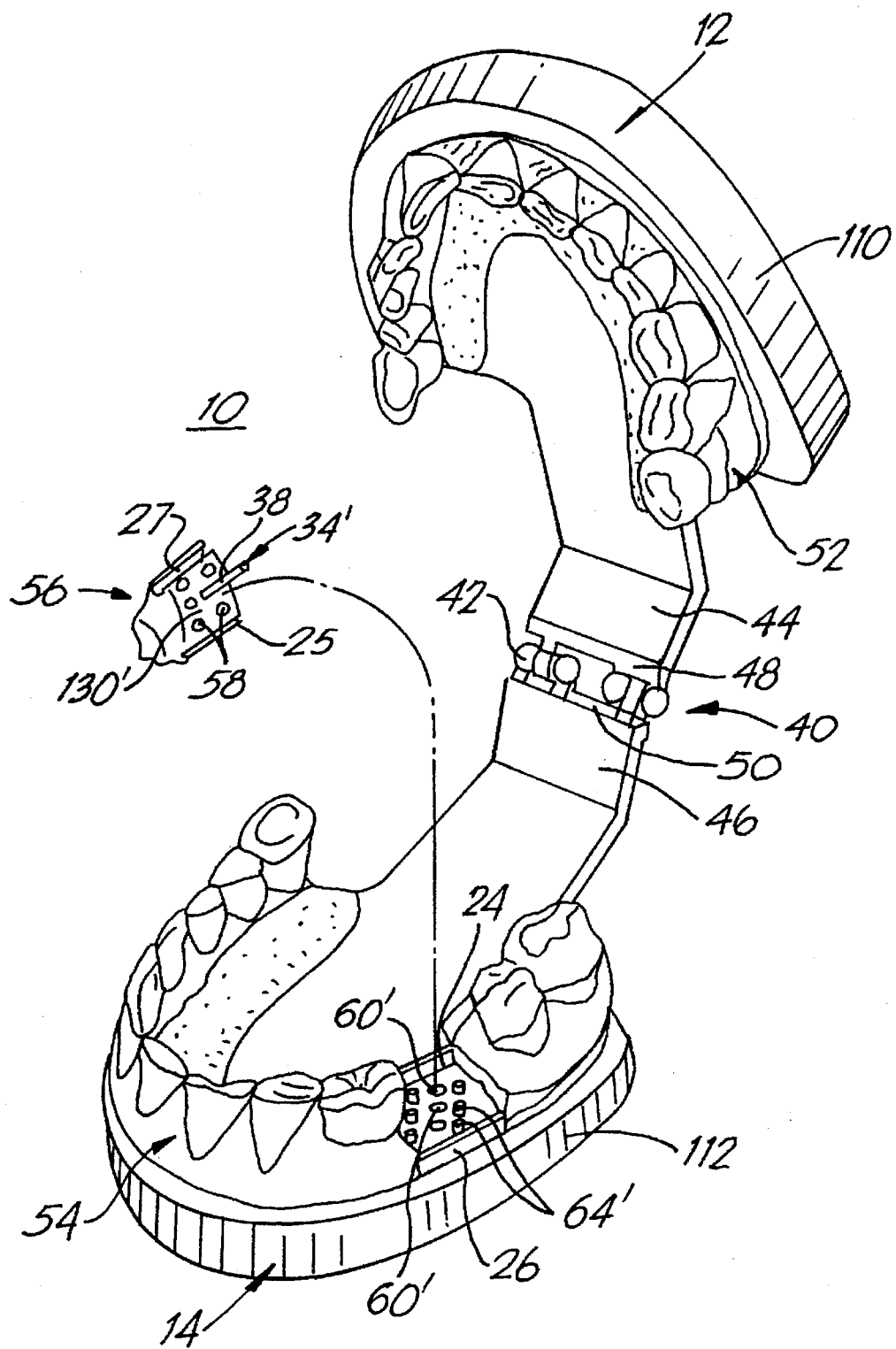
FIG. 3 is an exploded perspective view of the dental articulator lower arch showing the stone cast with an individual die removed (dental prosthetic being a crowned tooth) and having a dowel pin mounted within, and also showing the die holes and ridge indentations formed therein by the support pins and walled ridges.
Figure 4:
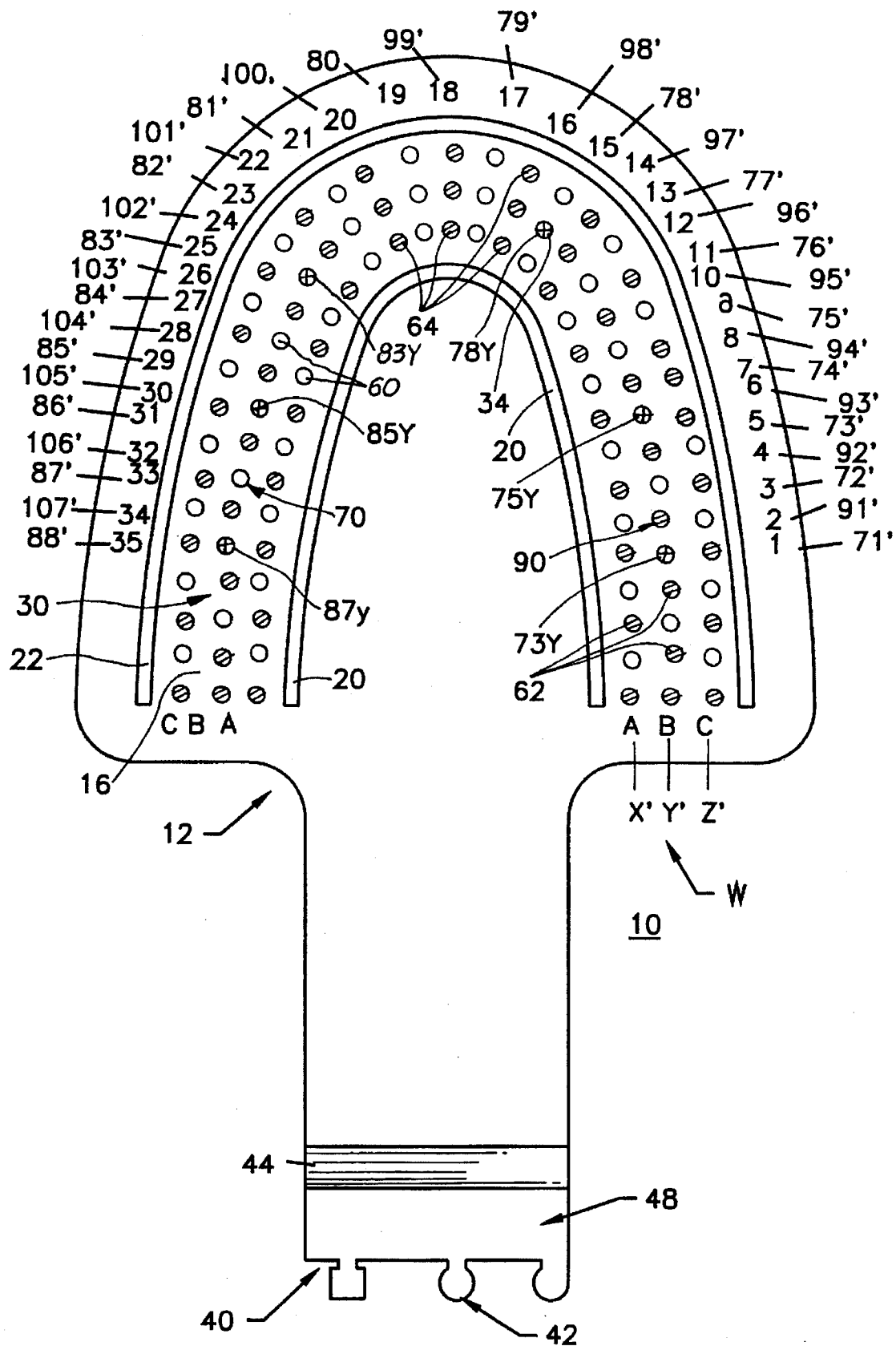
FIG. 4 is a top plan view of the dental articulator upper arch showing the support holes in the upper grid pattern for receiving the support pins, and the dowel pin holes for mounting the dowel pins on the upper die-receiving surface.
Figure 5:
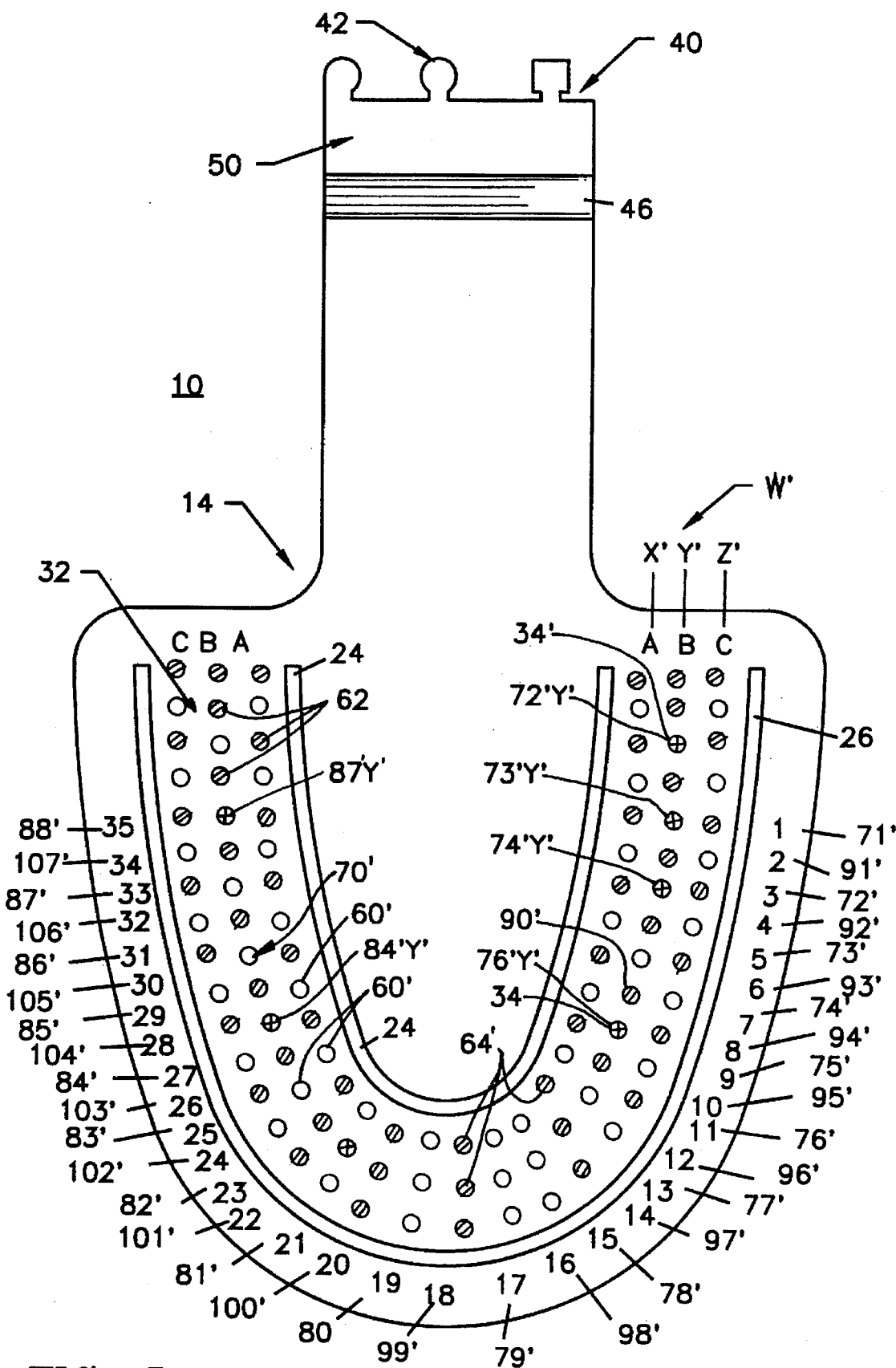
FIG. 5 is a top plan view of the dental articulator lower arch showing the support holes in the lower grid pattern for receiving the support pins, and the dowel pin holes for mounting the dowel pins on the lower die receiving surface.

The dental articulator 10 and its component parts of the preferred and alternate embodiments of the present invention are represented in detail by FIG. 1 through 15. The dental articulator 10 comprises an upper arch 12 and a lower arch 14 having upper and lower die-receiving surfaces 16, 18, respectively, that face each other. The upper and lower arches 12 and 14 have a U-shaped configuration with the material of construction being rigid plastic, rubber, a lightweight metal, or fiberglass. Such materials of construction may be phenolic plastic resins, chlorinated rubber, aluminum, or epoxies with woven glass. Also, located on the upper and lower die-receiving surfaces 16 and 18 are pairs of concentric U-shaped inner and outer ridges 20, 22, 24, and 26. On the upper die receiving surface 16, between the U-shaped inner and outer ridges 20 and 22 is an upper grid pattern space 30. Similarly, on the lower die-receiving surface 18, between the U-shaped inner and outer ridges 24 and 26 is a lower grid pattern space 32, as shown in FIGS. 1, 4, and 5.

The upper and lower arches 12 and 14 are detachably connected by a hinge 40 at a hinge location 42, such that upper arch 12 has an integrally connected upper hinge arm 44, and lower arch 14 has an integrally connected lower hinge arm 46. The upper hinge arm 44 is disposed at a 105° angle to the upper arch 12, while lower hinge arm 46 is disposed at a 105° angle to the lower arch 14. The hinge 40 has upper and lower hinge interlocks 48, 50; such that, the hinge interlocks 48 and 50 snap in place at hinge location 42, thus forming hinge 40, as depicted in FIGS. 1 to 6.

The upper and lower arches 12, 14 of articulator 10 receive upper and lower casts 52, 54. The casts 52, 54 are mold replications of the upper and lower teeth of a persons' jaw. In practice, the dental technician cuts the cast 52 and/or 54 to separate out and form the tooth or die 56 to be worked on, as depicted in FIGS. 2, 3, 7, and 8.

Grid pattern space 30 on upper die-receiving surface 16 includes a plurality of dowel holes 60 that are divided into diagonal rows 70, which rows are numbered 71, 72, 73, 74, 75, 76, 77, 78, 79, 80, 81, 82, 83, 84, 85, 86, 87, and 88; and lettered columns W being columns X, Y, and Z. Holes 60 arranged in rows 70 and columns W are positioned between the U-shaped inner and outer ridges 20 and 22 of grid pattern space 30 of upper arch 12, as depicted in FIG. 4.

Similarly, grid pattern space 32 on lower die-receiving surface 18 includes a plurality of dowel holes 60' that are divided into diagonal rows 70', which rows are numbered 71' through 88'; and lettered columns W' being columns X', Y', and Z'. Holes 60' arranged in rows 70' and columns W' are positioned between the U-shaped inner and outer ridges 24 and 26 of grid pattern space 32 of lower arch 14, as depicted in FIG. 5.

Figure 7:
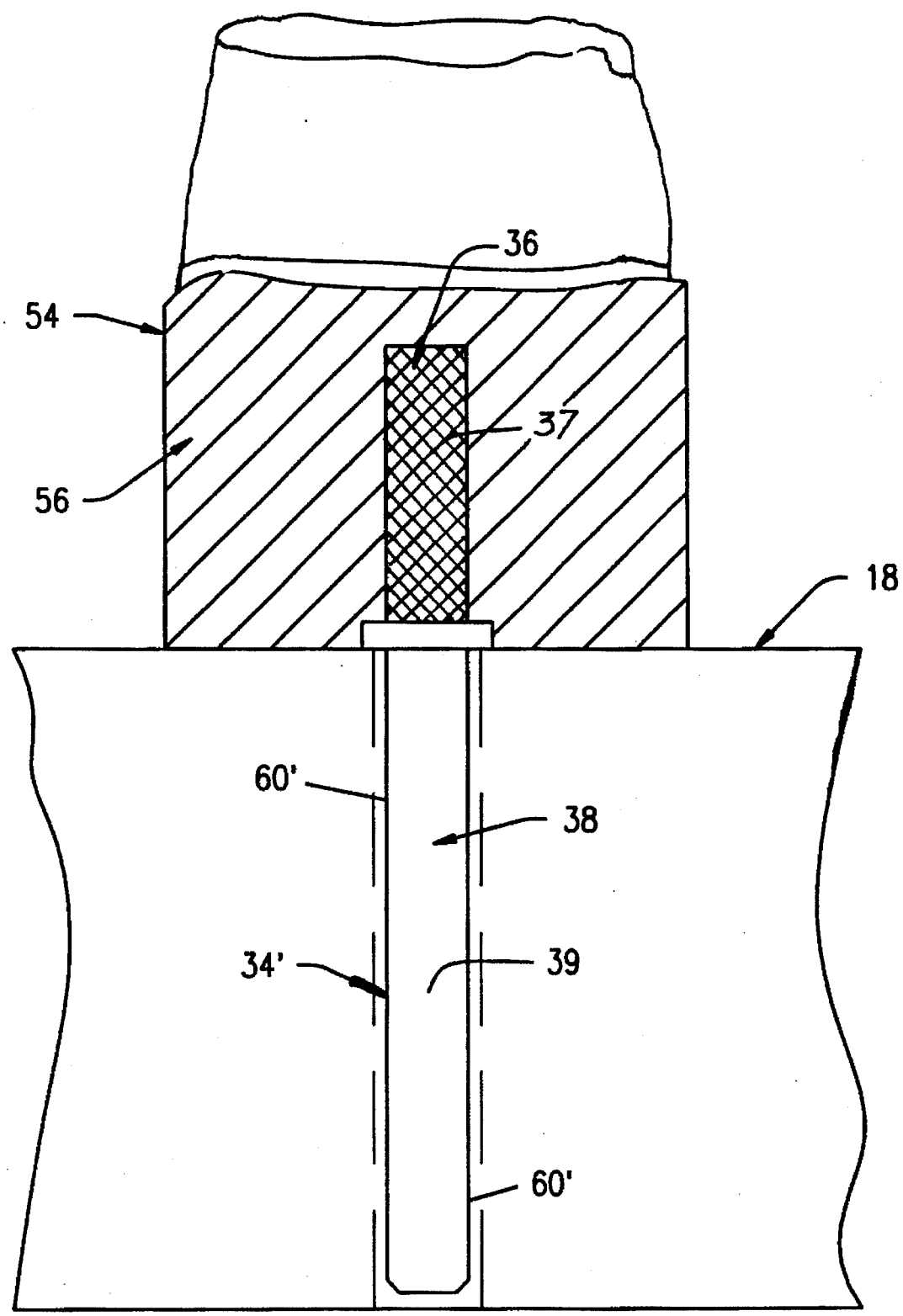
FIG. 7 is a side elevational view of the dowel pin showing its knurled section embedded in the lower cast/die and its smooth cylindrical section extending therefrom and releasably positioned within the dowel hole of the lower arch.

Dowel holes 60 and 60' are used to receive dowel pins 34, 34' which each have sections 36 and 38. Dowel pin 34 is an elongated brass or ceramic pin wherein section 36 has a knurled outer surface 37 which is embedded into the molded cast 52 or 54, as shown in FIG. 7. The other end of dowel pin 34 is a longer section 38, that has a smooth outer cylindrical surface 39 which is used in conjunction with a molded cast 54 and is for inserting into or removing from a dowel hole 60', as depicted in FIGS. 3 and 7.

Grid pattern 30 on upper die-receiving surface 16 also includes a plurality of support pin holes 62 having support pins 64 permanently mounted therein by means of epoxy glue. The support pins 64 are divided into diagonal rows 90, which rows are numbered 91, 92, 93, 94, 95, 96, 97, 98, 99, 100, 101, 102, 103, 104, 105, 106, and 107; and columns W being lettered columns X, Y, and Z. Support pins 64 are arranged in rows 90 and columns W where they are positioned between the U-shaped inner and outer ridges 20 and 22 of grid pattern space 30 of upper arch 12, as depicted in FIG. 4.

Similarly, grid pattern space 32 on lower die-receiving surface 18 also includes a plurality of support pin holes 62' having support pins 64' permanently mounted therein by means of epoxy glue. The support pins 64' are divided into diagonal rows 90', which rows are numbered 91' to 107'; and columns W' being lettered columns X', Y', and Z'Supports pins 64' arranged in rows 90' and columns W' are positioned between the U-shaped inner and outer ridges 24 and 26 of grid pattern space 32 of lower arch 14, as depicted in FIG. 5.

Figure 6:
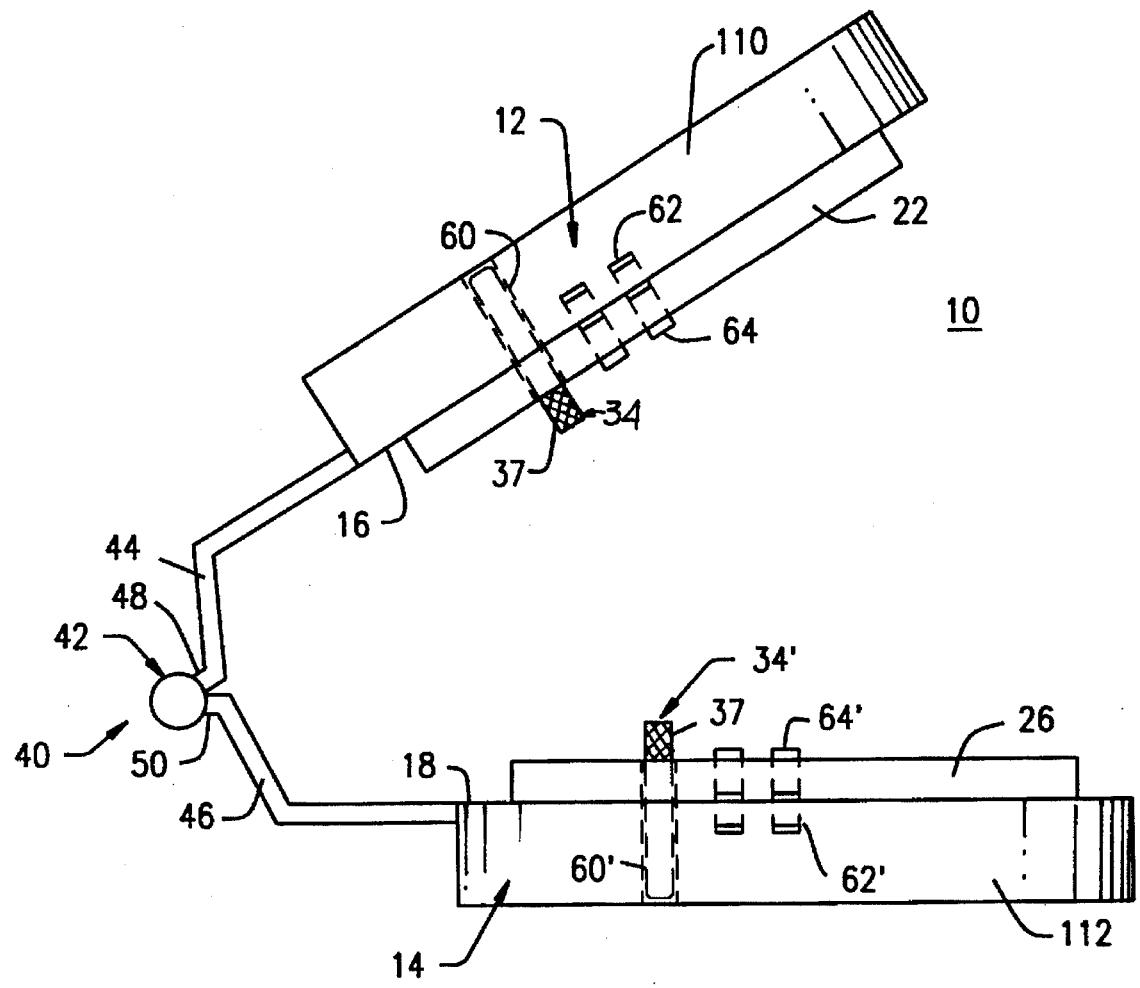
FIG. 6 is a side elevational view of the upper and lower arches showing the outer ridge, the support pins, and the dowel pins contained in the upper and lower die-receiving surfaces.
Figure 8:
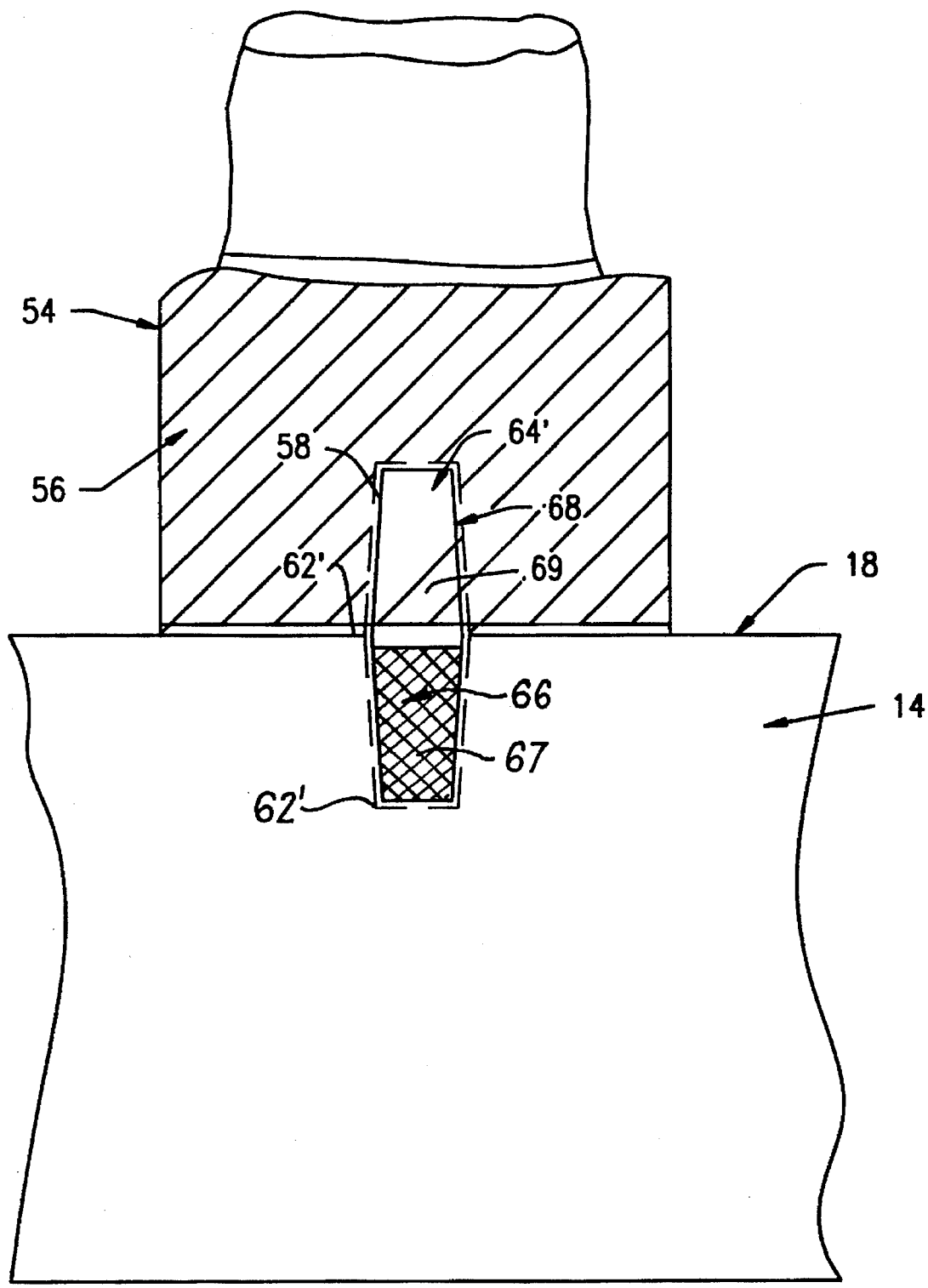
FIG. 8 is a side elevational view of the support pin showing its knurled section permanently embedded in the lower arch and its smooth cylindrical section extending therefrom for insertion in the die hole.

FIGS. 6 and 8 show support pin 64' having a first section 66 with a knurled outer surface 67 being firmly embedded in support pin hole 62' in the lower die-receiving surface 18 of lower arch 14. Extending upwardly from the die-receiving surface 18 is second section 68 of support pin 64' having a smooth cylindrical surface 69 for receiving lower cast 54 before it is hardened. After the lower cast 54 has hardened, the plurality of support pins 64' leave a plurality of die holes 58' formed or molded therein, as depicted in FIG. 3. Also, there are inner and outer ridge indentations 25, 27 formed therein from inner and outer ridges 24 and 26 after lower cast 54 has hardened in the prosthesis element 56, as shown in FIG. 3.

The dental articulator 10 in its assembled state in a closed mouth position, with casts 52 and 54 contained therein, has overall measurements being 70 mm in width by 95 mm in length by 50 mm in thickness. The upper and lower arches 12, 14 individually measure 70 mm in width by 60 mm in length by 10 mm in thickness. The upper or lower hinge arms 44, 46 of hinge 40 individually measure 20 mm in width having an overall length of 40 mm and 2 mm in thickness.

The pairs of concentric U-shaped inner and outer ridges 20, 22, 24, 26 of the upper and lower die-receiving surfaces 16 and 18 have an overall inner ridge 20 and 24 lengths of 80 mm and overall outer ridge 22 and 26 lengths of 125 mm with all ridge heights being 4 mm high and all ridge wall thicknesses being 1.25 mm thick. Upper or lower grid pattern space 30, 32 has an approximate overall area measurement of 1280 mm$^2$.

Dowel pin holes 60 and 60' measure 2 mm in diameter and support pin holes 62 and 62' measure 1.75 mm in diameter. Dowel pins 34 and 34' have a length of 14 mm by 2 mm in diameter, where the knurled first section 36 length is 3.5 mm and the smooth cylindrical second section 38 length is 10.5 mm. Support pins 64 and 64' have a length of 6 mm by 1.75 mm in diameter, where the knurled first section 66 length is 3 mm and the smooth cylindrical second section 68 length is 3 mm. All linear measurements have tolerances of ±1.0 mm; all diameter measurements have tolerances of ±0.1 mm; and all wall thicknesses have tolerances of ±0.1 mm.

Detailed Description of the Alternate Embodiment 200

An alternate embodiment 200 of the dental articulator 10 of the present invention is depicted in FIGS. 9 to 13. The functional aspects of the alternate dental articulator 200 are the same as the preferred embodiment of dental articulator 10, except for the overall shape, the grid patterns 30 and 32, and the inner and outer ridges 22, 24, 26, and 28 of the upper and lower arches 12 and 14, which are different.

Figure 9:
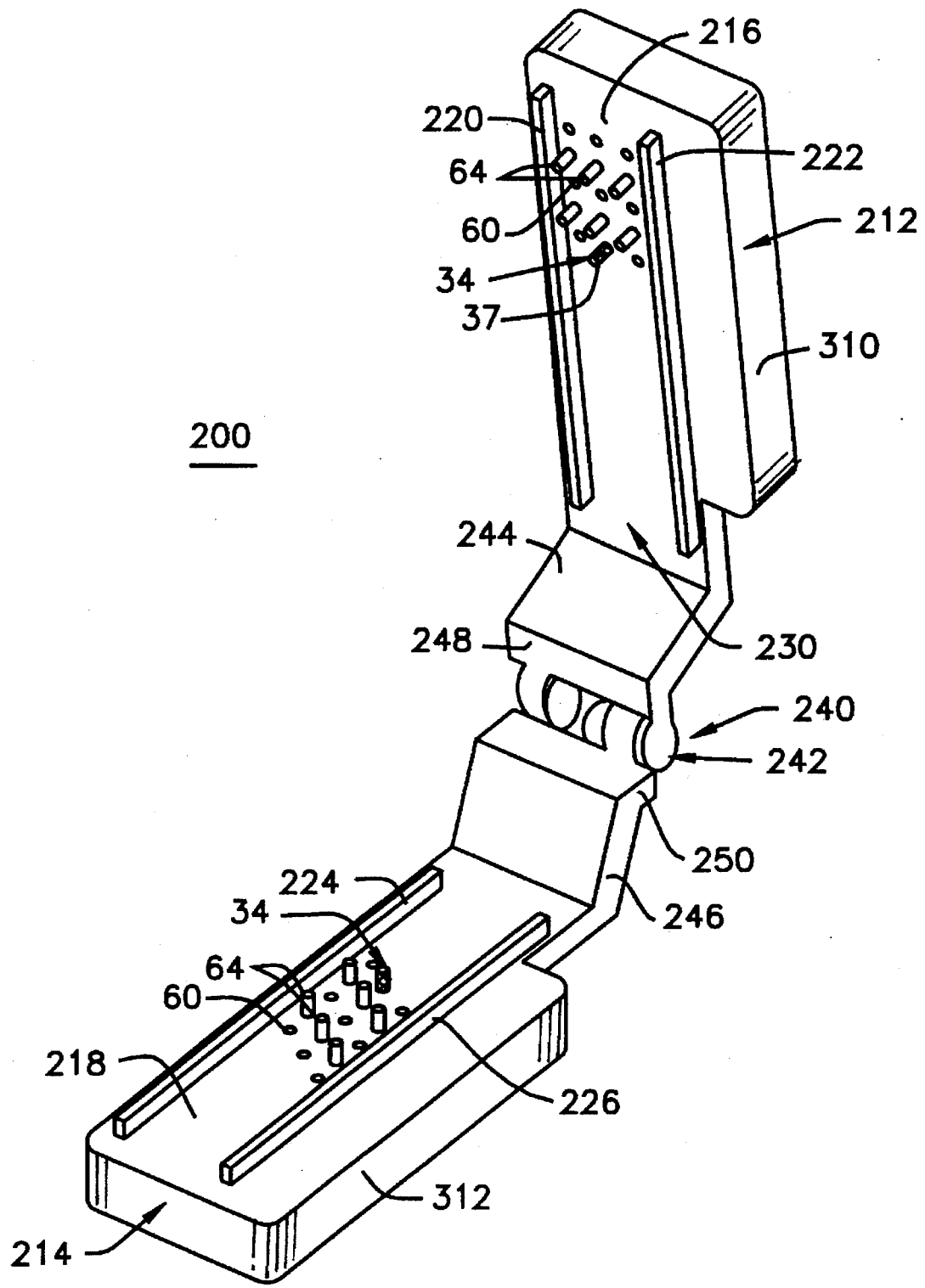
FIG. 9 is a perspective view of a second embodiment of a dental articulator of the present invention showing it in its assembled state.
Figure 11:
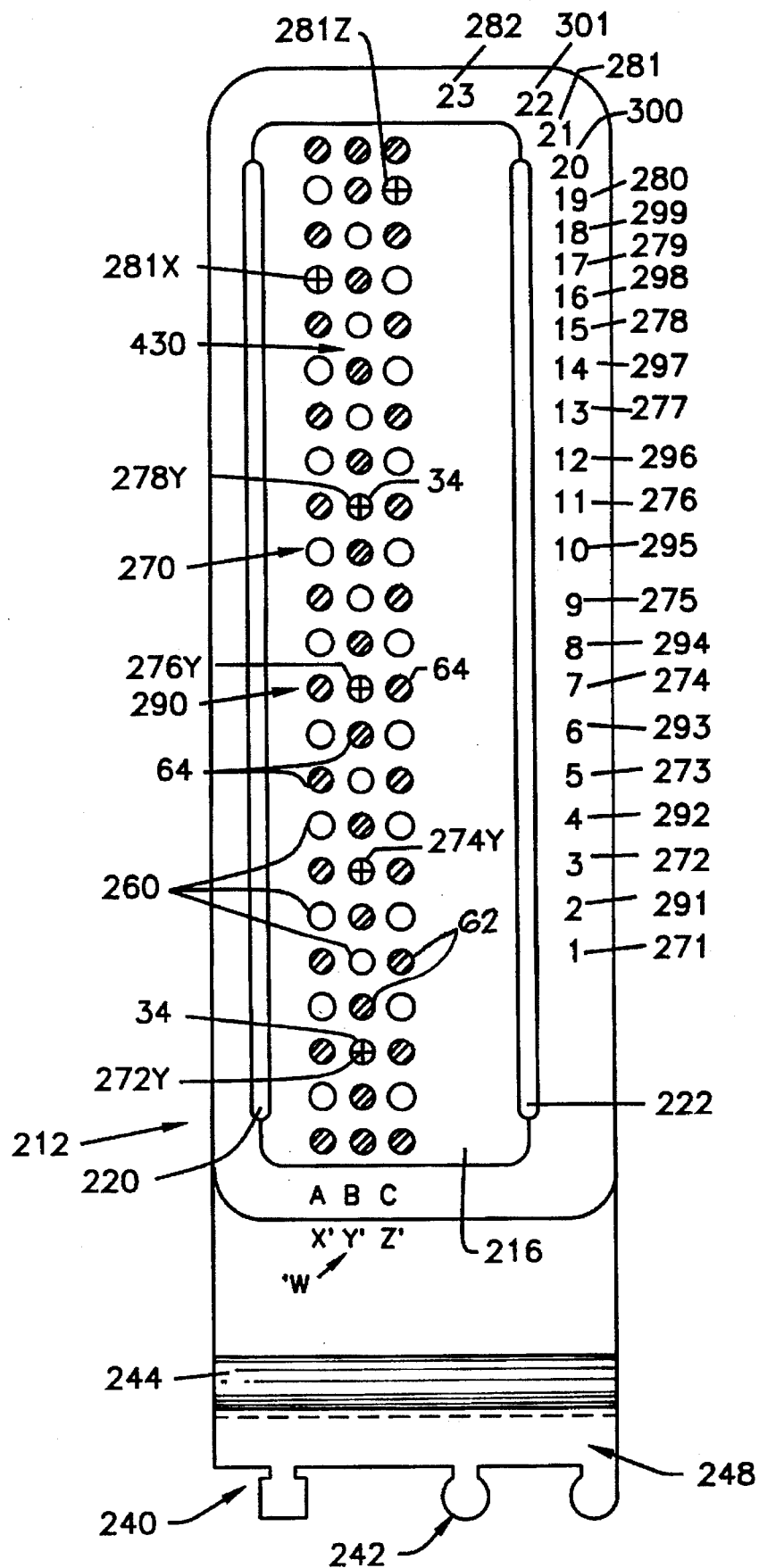
FIG. 11 is a top plan view of the second embodiment of the dental articulator upper arch showing the support holes in the upper grid pattern for receiving the support pins, and the dowel pin holes for mounting the dowel pins on the upper die-receiving surface.
Figure 12:
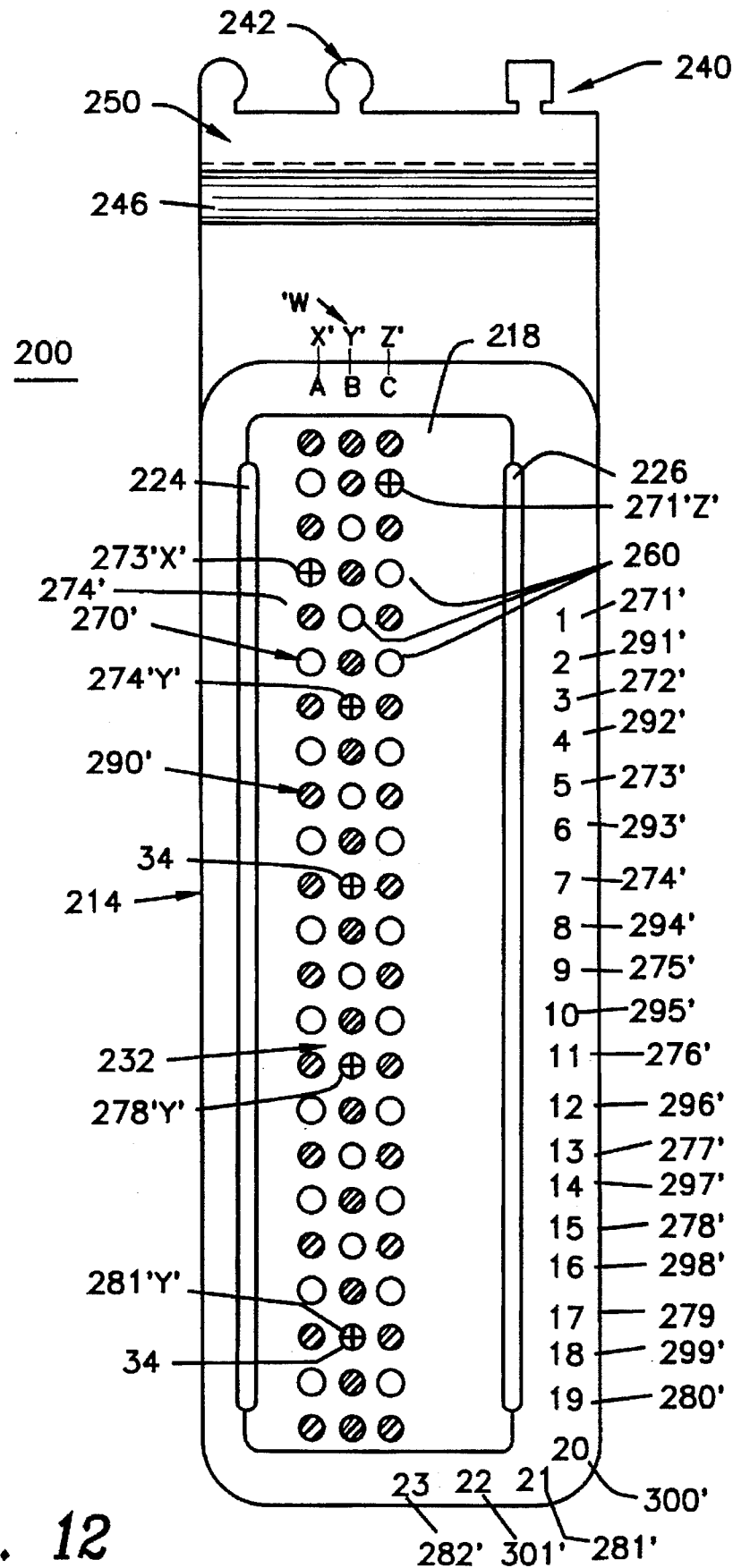
FIG. 12 is a top plan view of the second embodiment of the dental articulator lower arch showing the support holes in the lower grid pattern for receiving the support pins, and the dowel pin holes for mounting the dowel pins on the lower die-receiving surface.

Dental articulator 200 comprises upper and lower arches 212 and 214 having upper and lower die-receiving surfaces 216 and 218, respectively, that face each other. The upper and lower arches 212 and 214 are rectangular in configuration with materials of construction being rigid plastic, rubber, light-weight metals, or fiberglass. Such materials of construction can be phenolic plastic resins, chlorinated rubber, aluminum, or epoxies with woven-glass. Located on the upper and lower die-receiving surfaces 216 and 218 are a pair of parallel inner and outer ridges 220, 222, 224, and 226. On the upper die-receiving surface 216, between the parallel inner and outer ridges 220 and 222 is an upper grid pattern space 230. Similarly, on the lower die-receiving surface 218, between the parallel inner and outer ridges 224 and 226 is a lower grid pattern space 232, as shown in FIGS. 9, 11, and 12 of the drawings.

The upper and lower arches 212 and 214 are detachably connected by a hinge 240 at hinge location 242, such that, upper arch 212 has an integrally connected upper hinge arm 244, and lower arch 214 has an integrally connected lower hinge arm 246. The upper hinge arm 244 is disposed at a 105° angle to upper arch 212, while lower hinge arm 246 is disposed at a 105° angle to lower arch 214. The hinge 240 has upper and lower hinge interlocks 248 and 250, such that the hinge interlocks 248 and 250 snap in place at hinge location 242, thus forming hinge 240, as depicted in FIGS. 9, 11, 12, and 13.

The upper and lower arches 212 and 214 of articulator 200 receive upper and lower partial casts 252 and 254. The partial casts 252, 254 are mold replications of the upper and lower teeth of the person's jaw. In practice, the dental technician cuts the cast 252 and/or 254 to separate out and form (the tooth or teeth) die 256 to be worked on, as depicted in FIGS. 10 and 13.

Grid pattern space 230 on upper die-receiving surface 216 includes a plurality of dowel pin holes 260 that are divided into diagonal rows 270, which rows are numbered 271, 272, 273, 274, 275, 276, 277, 278, 279, 280, 281, and 282; and lettered columns W being columns X, Y, and Z. Dowel pin holes 260 arranged in rows 270 and columns W are positioned between the pair of parallel inner an outer ridges 220 and 222 of upper grid pattern space 230 of upper arch 212, as depicted in FIG. 11.

Similarly, grid pattern space 232 on lower die-receiving surface 218 includes a plurality of dowel pin holes 260' that are divided into diagonal rows 270', which rows are numbered 271' to 282'; and lettered columns W' being columns X'Y' and Z'. Dowel pin holes 260' arranged in rows 270' and lettered columns W' are positioned between the pair of parallel inner and outer ridges 224 and 226 of lower grid pattern space 232 of lower arch 214, as depicted in FIG. 12.

Figure 10:
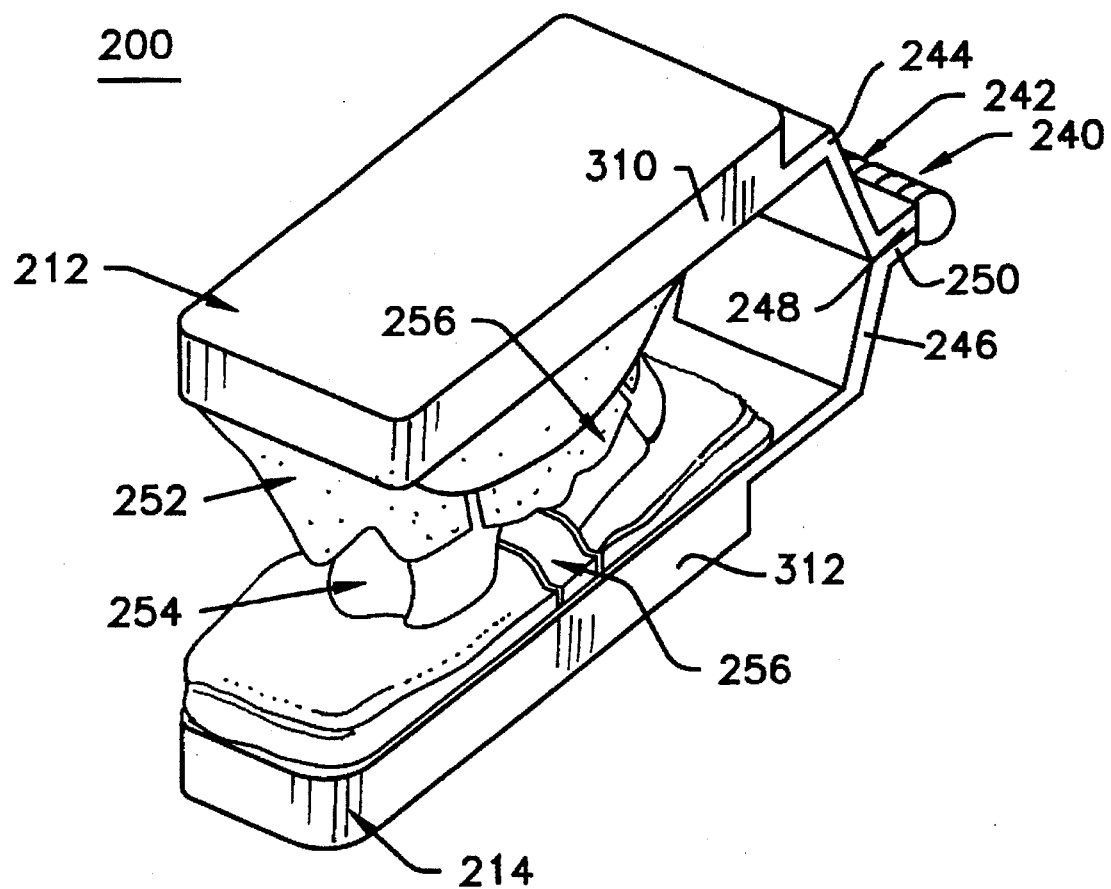
FIG. 10 is a perspective view of the second embodiment of the dental articulator having upper and lower stone casts contained therein and showing the cuts of an individual die.
Figure 13:
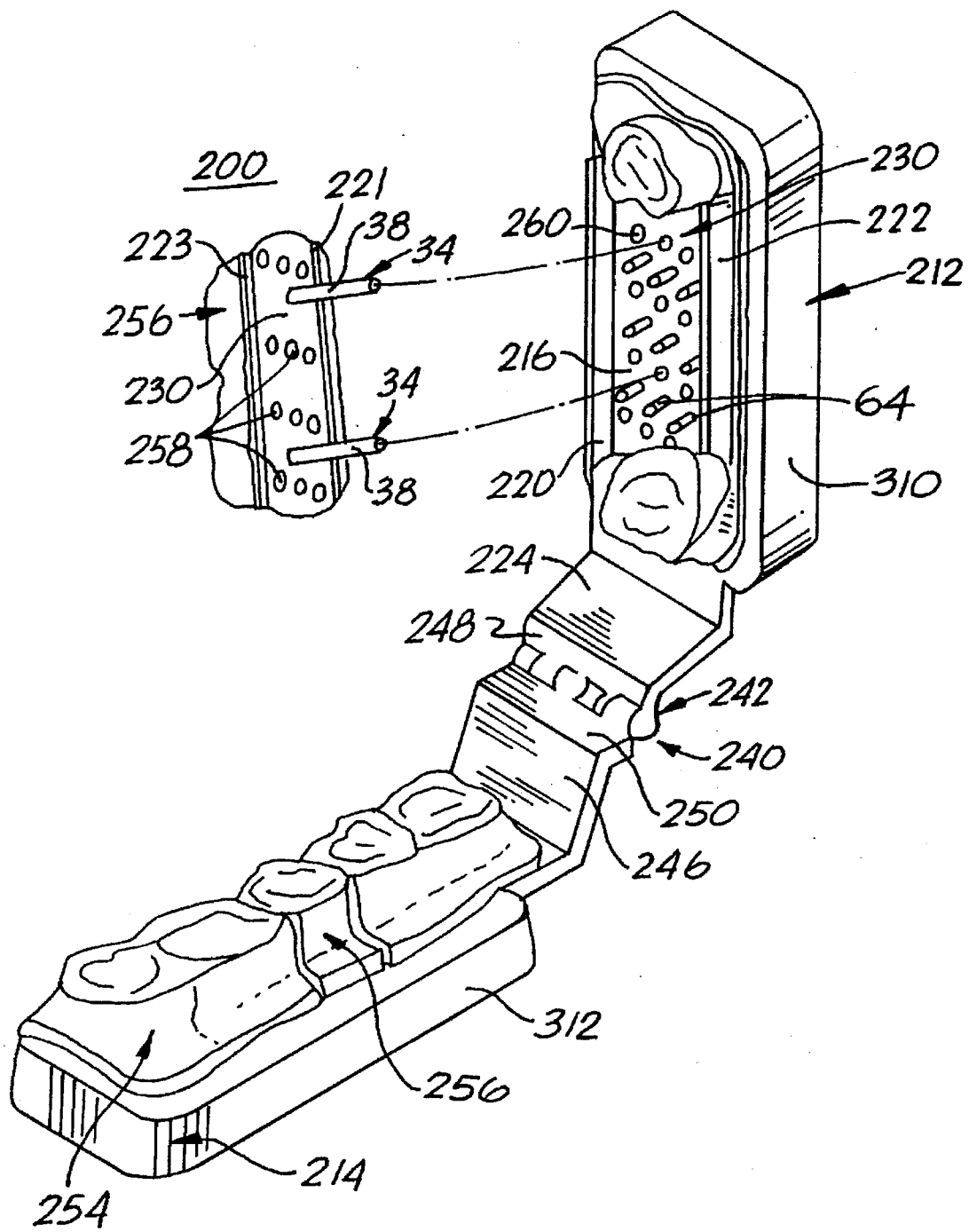
FIG. 13 is a bottom perspective view of the second embodiment of a die removed from the upper cast of FIG. 11 showing the die holes formed by the support pins.

Dowel pin holes 260 and 260' are used to receive the removable section 36 of dowel pins 34, whereas the embedded section 38 of dowel pins 34 are permanently attached to the partial casts 252 or 254, as depicted in FIGS. 10 and 13.

Grid pattern 230 on upper die-receiving surface 216 also includes a plurality of support pin holes 262 having support pins 64 permanently mounted therein by means of epoxy glue. The support pins 64 are divided into diagonal rows 290, which rows are numbered 291, 292, 293, 294, 295, 296, 297, 298, 299, 300, and 301; and lettered columns W being columns X, Y, and Z. Support pins 64 arranged in rows 290 and columns W are positioned between the pair of parallel inner and outer ridges 220 and 222 of grid pattern space 230 of upper arch 212, as depicted in FIG. 11.

Similarly, grid pattern 232 on lower die-receiving surface 218, also includes a plurality of support pins holes 262' having support pins 64' permanently mounted therein by means of epoxy glue. The support pins 64' are divided into diagonal rows 290', which rows are numbered 291' to 301'; and lettered columns W' being columns X', Y' and Z' Support pins 64' arranged in rows 290' and columns W' are positioned between the pair of parallel inner and outer ridges 224 and 226 of grid pattern space 232 of lower arch 214, as depicted in FIG. 12.

FIGS. 9 and 13 of the second embodiment 200, show the support pin 64 having a knurled first section 66 firmly embedded in the upper die-receiving surface 216 in support pin holes 262 in upper arch 212. Extending downwardly from the die-receiving surface 216 is the second section 68 for receiving an upper partial cast 252 before it is hardened. After the upper partial cast has hardened, the plurality of support pins 64 form a plurality of die holes 258 molded therein, as depicted in FIG. 13.

The dental articulator 200 in its assembled state in a closed mouth position, with casts 252 and 254 contained therein, has overall measurements being 25 mm in width by 90 mm in length by 50 mm in thickness. The upper or lower arches 212, 214 individually measure 25 mm in width by 70 mm in length by 10 mm in thickness. The upper or lower hinge arms 244, 246 of hinge 240 individually measure 20 mm in width having an overall length of 20 mm and 2 mm in thickness.

The pair or parallel inner and outer ridges 220, 222, 224, and 226 have an overall length of 57 mm with ridge heights being 4.0 mm high and ridge wall thicknesses being 1.25 mm thick. Upper or lower grid pattern space 230, 232 has an approximate overall area measurement of 712.5 mm$^2$.

All other measurements of dowel pin holes 60 and 60', support pin holes 62 and 62', dowel pins 34 and 34', and support pins 64 and 64' are the same as the preferred embodiment of dental articulator 10, as well as the tolerances previously mentioned.

Detailed Description of the Alternate Embodiment 400

Figure 14:
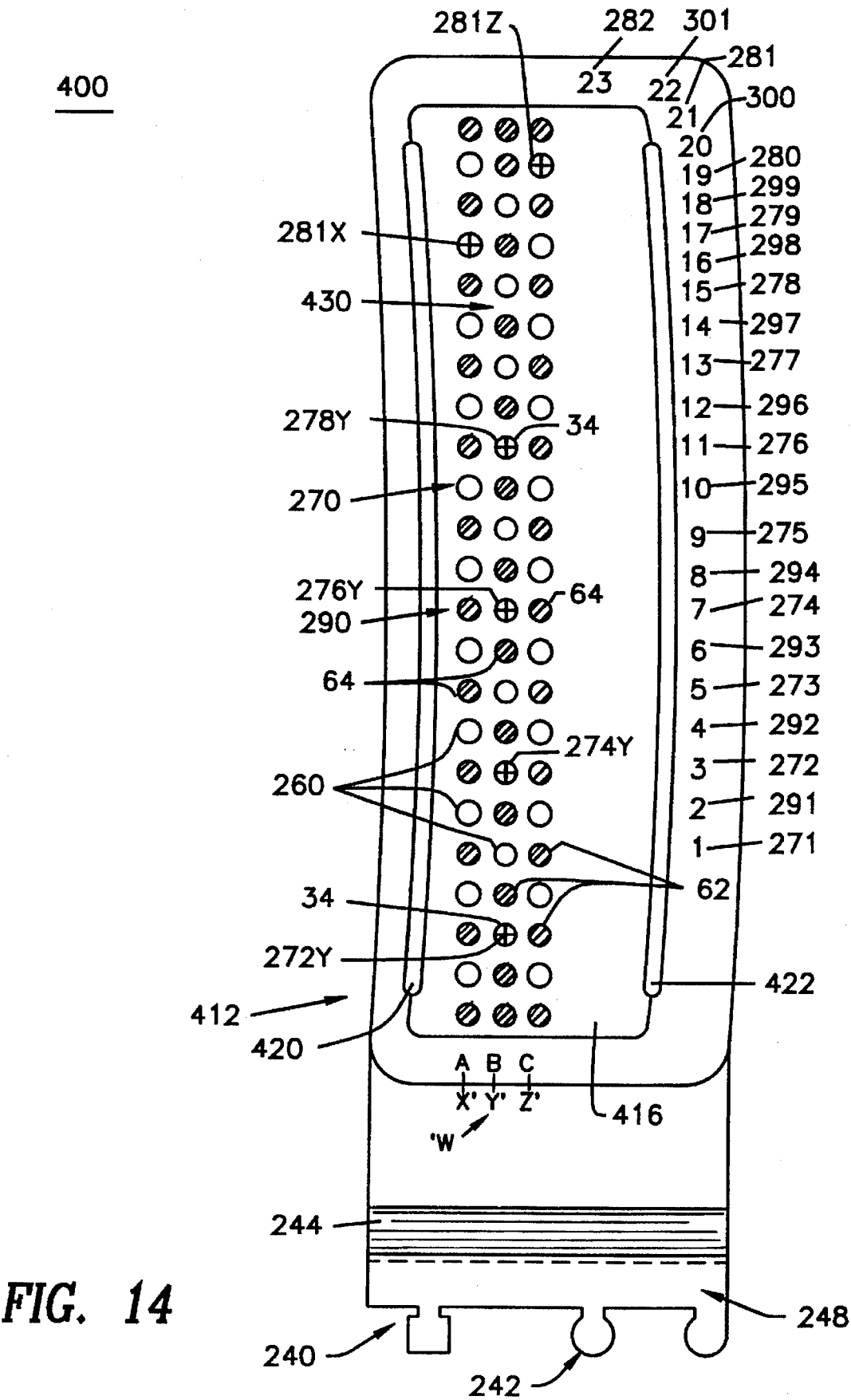
FIG. 14 is a top plan view of the third embodiment of the dental articulator showing a curved upper arch having support holes in the upper grid pattern for receiving the support pins, dowel pin holes for mounting the dowel pins on the upper die-receiving surface, and curved walled ridges for stone cast support.
Figure 15:
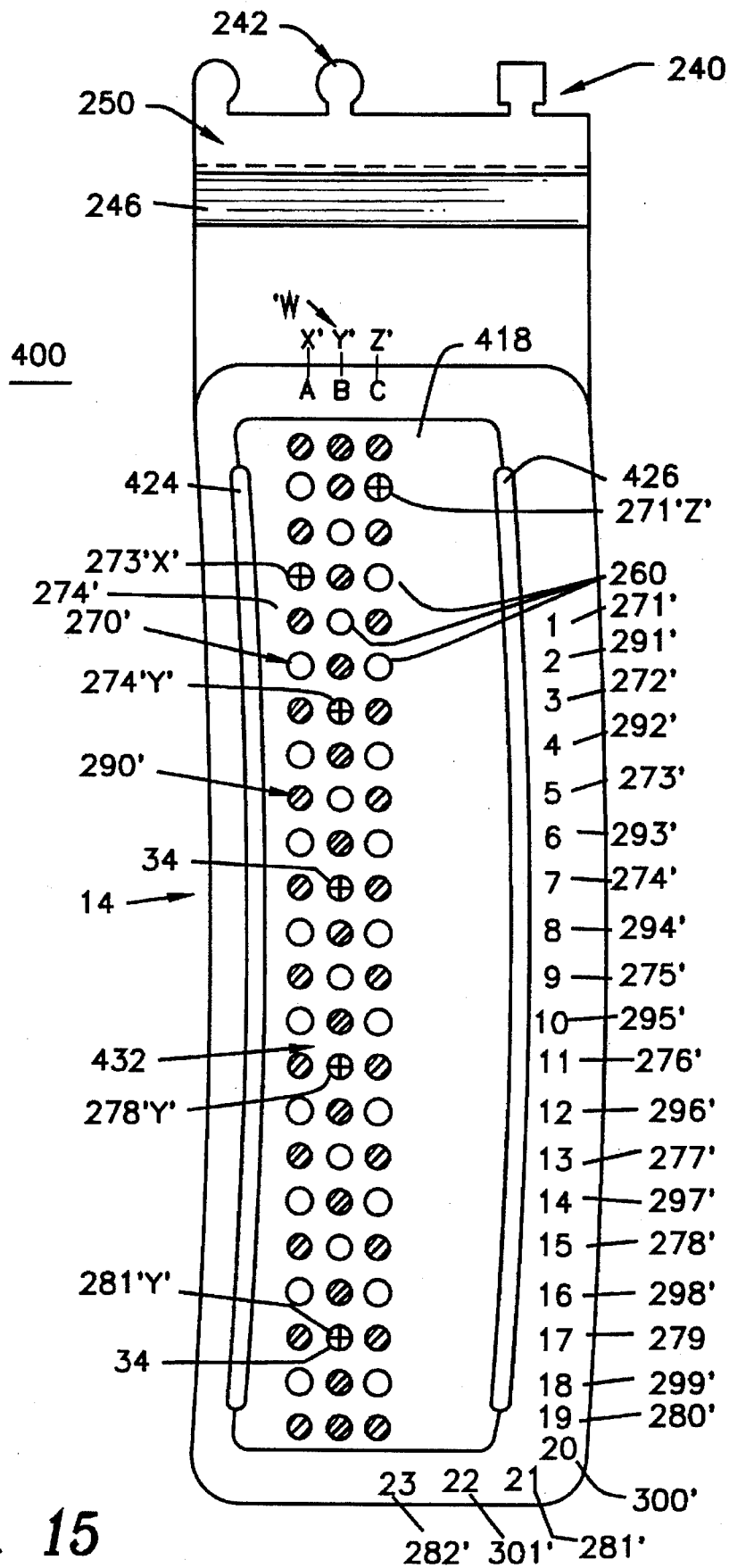
FIG. 15 is a top plan view of the third embodiment of the dental articulator showing a curved lower arch having support holes in the lower grid pattern for receiving the support pins, dowel pin holes for mounting the dowel pins on the lower die-receiving surface, and curved walled ridges for stone cast support.

A further embodiment 400 of the dental articulator 10 is depicted in FIGS. 14 and 15. The functional aspects of the additional dental articulator 400 are the same as the preferred dental articulator 10, except for the curved shapes of the upper and lower arches 412 and 414, curved upper and lower ridges 420, 422, 424, and 426, and curved shapes of grid pattern spaces 430 and 432 of die-receiving surfaces 416 and 418, which are different.

Operation of the Present Invention

The dental articulators 10, 200 and 400 of the present invention are designed to assist the dentist or dental technician with patient cases involving the use of closed-mouth impression techniques to produce a dental prosthesis, such as a crown or bridge. As known in the art, after the upper and lower mandible impressions are made by the dental technician, the top and bottom of the impressions are cut or sliced to produce a flat surface, in which dowel pins 34, 34' will be embedded. These dowel pins 34, 34' are placed in the appropriate locations in the upper and lower arch 12, 212, 14, 214 within the articulator 10, 200 or 400 to be used. For example, in FIGS. 4 and 5 of articulator 10, dowel pins 34, 34' are placed in the upper and lower grid patterns 30 and 32, respectively, in the appropriate locations.

For example, a row number 70, 70' and a column letter W, W' are used to define a dowel pin location, i.e. where 5B is indicated by the row number 5 and column letter B and lead line 73Y points to 5B, as shown in FIG. 4. Further examples, as shown in FIGS. 4 and 5, of locations of dowel pins 34, 34' are at 5B (73Y), 9B (75Y), 15B (78Y), 25B (83Y), 29B (85Y), and 33B (87Y) of upper arch 12; and at 3B (72'Y'), 5B (73'Y'), 7B (74'Y'), 11B (76'Y'), 21B (81'Y'), 27B (84'Y'), and 33B (87'Y') of lower arch 14.

In articulator 200, as shown in FIGS. 11 and 12, dowel pins 34 and 34' were placed in the upper and lower grid patterns 230 and 232, respectively, in the appropriate locations as depicted in row number 270, 270' and column letters W, W'. For example, in upper grid pattern 230, as depicted in FIG. 11, locations of dowel pins 34 are at 3B (272Y), 7B (274Y), 11B (276Y), 15B (278Y), 21A (281X), and 21C (281Z) for upper arch 212; and in lower grid pattern 232, as depicted in FIG. 12, locations of dowel pins 34' are at row and column numbers 1C (271'Z'), 5A (273'X'), 7B (274'Y'), 11B (276'Y'), 15B (278'Y'), and 21B (281'Y') for lower arch 214. The dental technician notes the dowel pin 34, 34' locations of each articulator to insure the stability of die 56 and 256 after cutting, such that dowel pins 34 and 34' are centrally located in the bottom of dies 56 and 256, as shown in FIGS. 3 and 13.

The dental technician then pours stone for forming the die in the lower arch 14 or 214 which covers the dowel pins 34', the support pins 64' and the ridges 24 and 26 or 224 and 226. In doing this, he/she utilizes a guide mark put on the lower cast impression 54, 254 and uses a guide mark put on lower arch 14, 214 outer wall/side wall 112, 312. These guide marks are aligned and allow the cast 54 or 254 to be centered on the lower arch 14 or 214. This step is repeated for the upper arch 12 or 212, wherein the technician pours stone for forming the die which covers the dowel pins 34, the support pins 64 and the ridges 20, 22 and 220, 222. In doing this, he/she utilizes a guide mark put on outer wall 110 or side wall 310 of upper arch 12 or 212. These guide marks are aligned and allow the cast 52 or 252 to be centered on the upper arch 12 or 212, as shown in FIGS. 2, 3, and 10.

Figure 2:
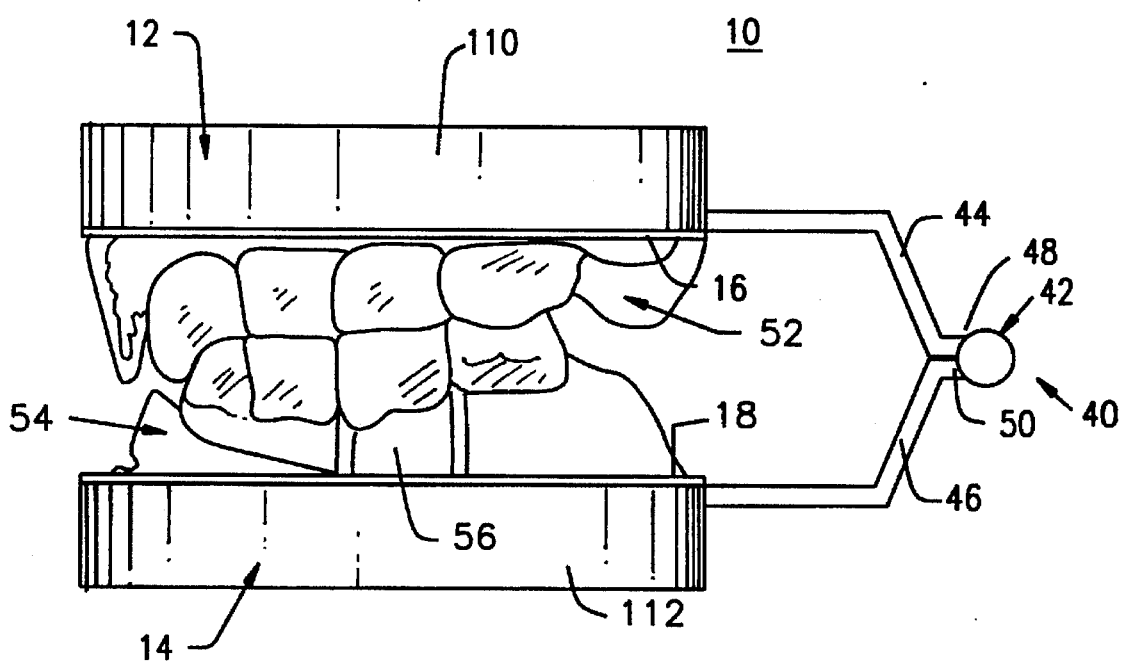
FIG. 2 is a side view of the dental articulator having upper and lower stone casts contained therein and showing the cuts of an individual die.

After the stone has been poured for the dental articulator 10 and 200, it is moved to a closed position, as shown in FIGS. 2 and 11. After the stone has hardened, the individual dies 56 or 256 are cut or sawed, and these individual dies 56 or 256 which have been cut can then be removed from the upper and/or lower arches 12, 14, 212, or 214 to be worked on by the dental technician.

FIGS. 3 and 13 show a die 56 and 256 removed from arch 14 and 212, and in particular, the bottom surface 130', 230 thereof, having a dowel pin 34', 34 extending therefrom, and a plurality of support holes 58', 258 formed in the bottom surface 130', 230 of the die 56 and 256; which surround the dowel pin 34', 34. In this manner, when the die 56, 256 is placed on the arch 14, 212, the support pins 64', 64 are inserted into respective support holes 58', 258, and the dowel pins 34', 34 are inserted into respective dowel holes 60' and 60. As a result, the individual die 56, 256 is securely held in place and cannot shift, move or rotate while being worked on, which increases the accuracy of the fit in the patients mouth.

This holding feature is supplemented by the inner and outer ridges 20, 22, 24, and 26 or 220, 222, 224, and 226 which also act to prevent shifting, movement or rotation of the die 56, 256. As shown in FIGS. 9 and 15, the inner and outer ridges 24 and 26; 220 and 222; form grooves 25 and 27 or grooves 221 and 223 in the bottom surface 130' or 230 of die 56, 256 which also act to hold those dies more securely in place.

This aforementation stabilization of the die 56, 256 enables the dental technician to work with greater accuracy on the dental prosthetic of a bridge or crown, without any rotation or movement of that die. This results in less time needed for the dentist to work in a patients' mouth to fit the prosthetic element.

Advantages of the Present Invention

Accordingly, an advantage of the present invention is that it provides a dental articulator that more securely holds the prosthesis die element being worked on, such that there is no rocking or shifting movement of the prosthesis die element being worked on.

Another advantage of the present invention is that it provides a dental articulator that increases the accuracy of construction of the prosthesis die element being worked on with a minimal amount of time, labor, and cost thereby minimizing the patients' dental costs.

Another advantage of the present invention is that is provides a dental articulator apparatus that is easy to handle and work with, and that is light weight, durable and universal, such that the articulator can be used for various types of dental prosthesis elements, such as, crowns, caps, bridges, inlays, onlays, and the like.

A further advantage of the present invention is that provides a dental articulator that can be mass produced in an automated and economical manner, and is also cost effective.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A dental articulator, comprising:
   a) a first arch for receiving a dental cast of teeth having a first grid pattern that includes a first plurality of dowel pin holes that define multiple dowel pin locations for receiving a first plurality of dowel pins, and a first plurality of support pin holes that define multiple support pin locations for receiving a first plurality of support pins, said dowel pin locations and said support pin locations being spaced apart such that a die may be held in place within said first arch by one or more of said first plurality of dowel pins and by one or more of said first plurality of support pins to prevent movement or rotation of said die; said first support pin holes having permanently mounted therein said first support pins;
   b) a second arch for receiving a dental cast of teeth having a second grid pattern that includes a second plurality of dowel pin holes that define multiple dowel pin locations for receiving a second plurality of dowel pins, and a second plurality of support pin holes that define multiple support pin locations for receiving a second plurality of support pins, said dowel pin locations and said support pin locations being spaced apart such that a die may be held in place within said second arch by one or more of said second plurality of dowel pins and by one or more of said second plurality of support pins to prevent movement or rotation of said die; said second support pin holes having permanently mounted therein said second support pins; and
   c) said first arch being hingedly connected to said second arch by a hinge connection to allow articulating movement of said first and second arches with respect to each other.

2. A dental articulator in accordance with claim 1, wherein each of said first and second arches have a die receiving surface and wherein said die receiving surfaces each have inner and outer ridges for forming grooves in said die, and wherein said grooves receive said inner and outer ridges for providing additional support to said die to prevent movement or rotation thereof.

3. A dental articulator in accordance with claim 2, wherein said inner and outer ridges are arranged in a U-shaped configuration on the die-receiving surface of said first arch; and wherein said inner and outer ridges are arranged in a U-shaped configuration on the die-receiving surface of said second arch.

4. A dental articulator in accordance with claim 3, wherein said first grid pattern is U-shaped and is positioned between said U-shaped configuration of said inner and outer ridges of the die-receiving surface of said first arch; and wherein said second grid pattern is U-shaped and is positioned between said U-shaped configuration of said inner and outer ridges of the die-receiving surface of said second arch.

5. A dental articulator in accordance with claim 2, wherein said inner and outer ridges are arranged in a parallel configuration on the die-receiving surface of said first arch; and wherein said inner and outer ridges are arranged in a parallel configuration on the die-receiving surface of said second arch.

6. A dental articulator in accordance with claim 5, wherein said first grid pattern is rectangular in shape and is positioned between said pair of parallel inner and outer ridges of the die-receiving surface of said first arch; and wherein said second grid pattern is rectangular in shape and is positioned between said pair of parallel inner and outer ridges of the die-receiving surface of said second arch.

7. A dental articulator in accordance with claim 2, wherein said inner and outer ridges are arranged in a curved configuration on the die-receiving surface of said first arch; and wherein said inner and outer ridges are arranged in a curved configuration on the die-receiving surface of said second arch.

8. A dental articulator in accordance with claim 7, wherein said first grid pattern is curved and is positioned between said curved configuration of said inner and outer ridges of the die-receiving surface of said first arch; and wherein said second grid pattern is curved and is positioned between said curved configuration of said inner and outer ridges of the die-receiving surface of said second arch.

9. A dental articulator in accordance with claim 1, wherein said first grid pattern includes first alternating rows of said first dowel pin holes and said first support pin holes, and wherein said second grid pattern includes second alternating rows of said second dowel pin holes and said second support pin holes.

10. A dental articulator in accordance with claim 9, wherein said first alternating rows are arranged diagonally relative to said first arch; and wherein said second alternating rows are arranged diagonally relative to said second arch.

11. A dental articulator in accordance with claim 1, wherein said dental articulator is made from the group consisting of plastic, aluminum, rubber, and fiberglass.

12. A dental articulator in accordance with claim 1, wherein said first and second dowel pins are made from the group consisting of brass, aluminum, stainless steel, and ceramic.

13. A dental articulator in accordance with claim 12, wherein said first and second dowel pins each have a knurled, cylindrical first section for embedding said dowel pins in said die of said dental cast or teeth.

14. A dental articulator in accordance with claim 13, wherein said first and second dowel pins each have an elongated cylindrical second section for detachably inserting and retracting said first and second dowel pins in said respective first and second dowel pin holes.

15. A dental articulator in accordance with claim 1, wherein said first and second support pins are made from the group consisting of brass, aluminum, stainless steel, and ceramic.

16. A dental articulator in accordance with claim 15, wherein said first and second support pins have a knurled, cylindrical first section for embedding said first and second support pins in said respective first and second support pin holes.

17. A dental articulator in accordance with claim 15, wherein said first and second support pins have a cylindrical second section for forming die holes in said die; and wherein said die holes receive said first and second support pins.

18. A dental articulator in accordance with claim 1, wherein said first and second support pins are secured in said respective first and second support pin holes by epoxy glue.

19. A dental articulator in accordance with claim 1, wherein said hinge connection has a first support arm that forms at least a 90° angle relative to said second arch, and has a second support arm.

20. A dental articulator in accordance with claim 19, wherein said first and second support arms are detachably connected to each other at said hinge connection.

21. A dental articulator, comprising:

a) a first arch for receiving a dental cast of teeth having a first grid pattern that includes a first plurality of dowel pin holes that define multiple dowel pin locations for receiving a first plurality of dowel pins, and a first plurality of support pin holes that define multiple support pin locations for permanently receiving a first plurality of support pins, said dowel pin locations and said support pin locations being spaced apart, such that a die may be held in place within said first arch by at least one dowel pin and by at least two support pins to prevent movement or rotation of said die; said first support pin holes having permanently mounted therein said first support pins;

b) a second arch for receiving a dental cast of teeth having a second grid pattern that includes a second plurality of dowel pin holes that define multiple dowel pin locations for receiving a second plurality of dowel pins, and a second plurality of support pin holes that define multiple support pin locations for permanently receiving a second plurality of support pins, said dowel pin locations and said support pin locations being spaced apart, such that a die may be held in place within said second arch by at least one dowel pin and by at least two support pins to prevent movement or rotation of said die; said second support pin holes having permanently mounted therein said second support pins; and c) said first arch being hingedly connected to said second arch by a hinge connected to allow articulating movement of said first and second arches with respect to each other.

22. A dental articulator in accordance with claim 21, wherein a die is held in place by at least one dowel pin and by at least four support pins to prevent movement or rotation of said die.

* * * * *